United States Patent [19]

Doumit

[11] Patent Number: 5,453,005
[45] Date of Patent: Sep. 26, 1995

[54] SAFETY DEVICE FOR ORTHODONTIC APPARATUS

[76] Inventor: Amid Doumit, 44, rue Crozatier, 75012 Paris, France

[21] Appl. No.: 170,874

[22] Filed: Dec. 21, 1993

[30]   Foreign Application Priority Data

Dec. 21, 1992 [FR]   France .................... 92 15407

[51] Int. Cl.$^6$ .................................................... A61C 7/00
[52] U.S. Cl. ........................................................... 433/5
[58] Field of Search ................................................ 433/5, 17

[56]   References Cited

U.S. PATENT DOCUMENTS

| | | | |
|---|---|---|---|
| 3,903,604 | 9/1975 | Snead | 433/5 |
| 4,038,754 | 8/1977 | Armstrong | 433/5 |
| 4,087,915 | 5/1978 | Andrews | 433/5 |
| 4,212,637 | 7/1980 | Dougherty et al. | 433/5 |
| 4,453,917 | 6/1984 | Nodai et al. | 433/5 |
| 4,718,848 | 6/1988 | Hickham et al. | 433/5 |

*Primary Examiner*—Cary E. O'Connor
*Attorney, Agent, or Firm*—Pollock, Vande Sande & Priddy

[57]   ABSTRACT

Safety device for an orthodontic apparatus including an inner arch having ends that engage rings fixed on the molars and an outer arch having ends that are hooked to elastic bands fixed to an occipital system. The arch assembly is made up of two thin and integral metal tubes intersecting in front of the wearer's mouth. Inside the metal tubes, flexible metal wires of high strength slide. One connects the left elastic band to the right molar and the other connects the right elastic band to the left molar. The inner ends of the two wires remain latched to the teeth until the elastic bands are detached.

8 Claims, 2 Drawing Sheets

SAFETY DEVICE FOR ORTHODONTIC APPARATUS

FIELD OF THE INVENTION

The present invention relates to a safety device for apparatuses exerting extra-oral force; more precisely, this device has the aim of preventing the accidents which can occur in the event of the facial arch being withdrawn prior to the unhooking of the elastic bands.

BACKGROUND OF THE INVENTION

It is known that the orthodontic apparatuses exerting extra-oral force are made up of two integral metal arches, of which one, intra-oral, engages rings fixed on the molars and the other, extra-oral, is held on the occiput or the nape of the neck by virtue of a system of elastic bands.

Although this type of apparatus has been known since the last century, the use thereof has been suspended in France (degree of 22nd January 1992) following a number of serious accidents; indeed, if the user dismantles his apparatus by removing the inner arch from its fixing rings on the molars (then taking it out of his mouth) before the elastic bands of the outer arch have been unhooked, and if he then accidently lets go of the inner arch, the latter returns violently to its initial position, causing injuries in the mouth (or to the face).

Systems are already known which make it possible to reduce the risks mentioned hereinabove; for example, the U.S. Pat. No. 4,718,848 (HICKHAM) describes an attachment— consisting of a cord and of two hooks—which limits the possible travel of the facial arch at the moment of unhooking; and the U.S. Pat. No. 4,212,637 (DOUGHERTY) which describes a removable attachment between the two arches may also be mentioned; however, the known devices make it possible to reduce the risks of an accident, without completely eliminating it, in contrast to the present invention which provides total safety.

BRIEF DESCRIPTION OF THE INVENTION

The invention thus aims to prevent completely the removal of the inner arch from the rings prior to the unhooking of the elastic bands.

According to the invention, a safety device for apparatuses exerting an extra-oral force, comprising an inner arch whose ends engage rings fixed on the molars and an outer arch whose ends are hooked to elastic bands fixed to an occipital system, is characterized in that the arch assembly is made up of two thin and integral metal tubes intersecting in front of the mouth, inside which metal tubes there may slide two flexible, high-strength metal wires, one connecting the left elastic band to the right molar and the other connecting the right elasticsband to the left molar, the inner ends of the two wires latch to the teeth until the elastic bands are detached.

According to the invention, the fixing of the two metal tubes at their intersection is dismountable, in such a manner that, for a given total length of each tube, the two parts of the tube which are situated on each side of the intersection have adjustable lengths.

According to the invention, the said lock is obtained by means of a stud, which is integral with the inner end of each wire, protruding from a notch formed in each tube between its inner end and the sheath mounted on the ring to be fixed to the molar when the wire and the stud are subjected to the traction of the elastic band, whereas the stud withdraws into the inner end of the tube when the elastic band does not exert any traction.

The withdrawal of the stud is effected by means of a small spring mounted at the outer end of the corresponding wire.

The small spring can also be mounted inside the tube.

According to a variant of the invention, the lock is obtained by means of a substantially cylindrical and elastic small sleeve, mounted on the inner end of each wire between a terminal collar and the sheath mounted on the ring to be fixed to the molar, the diameter of the said small sleeve at rest being smaller than that of the said sheath, whereas its diameter under the action of the compression due to the extra-oral force is greater than that of the said sheath.

According to another variant of the invention, the latch is obtained by means of a metal loop provided at the inner end of the wire, this loop having a transverse dimension slightly smaller than the internal diameter of the corresponding tube, and moving transversely in cooperation with a bevelled section of the said end.

That part of the tubes which is situated towards the elastic bands for hooking is preferably partially slit at various positions in order to make it easier to cut to the desired length at the moment when the apparatus is positioned in the mouth.

It will be understood that the device, which forms the subject-matter of the invention, provides total safety since it is impossible to unlatch the inner arch, and thereby remove it from the mouth, without first having unhooked the elastic bands which exert the latching force.

Exemplary embodiments of the invention will be described, by way of non-limiting examples, with reference to the attached drawing, in which:

DETAILED DESCRIPTION OF THE INVENTION

Figure 1:
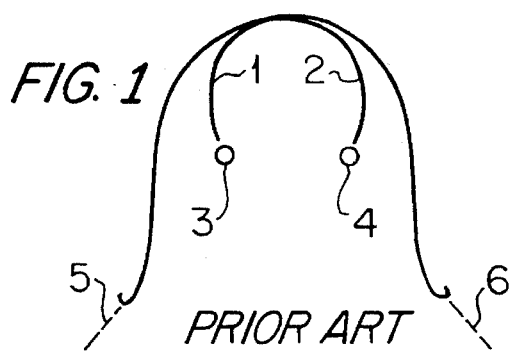
FIG. 1 is a diagram illustrating the prior art.

As is seen in FIG. 1, the known orthodontic apparatuses exerting extra-oral force are made up of two integral metal arches 1 and 2 of which one, intra-oral 1, engages rings 3 and 4 fixed on the molars (not shown) of the patient, and the other, extra-oral 2, is held on the occiput or the nape of the neck by virtue of a system of elastic bands 5 and 6.

Figure 2:
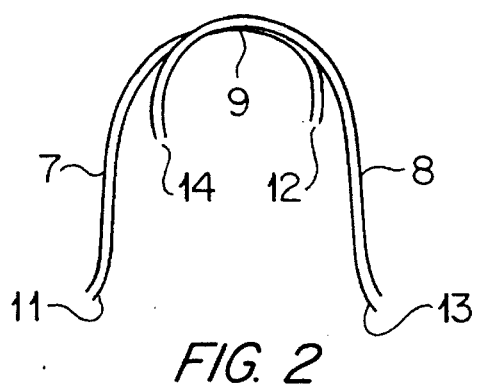
FIG. 2 is a diagram illustrating the principle of the invention.
Figure 3:
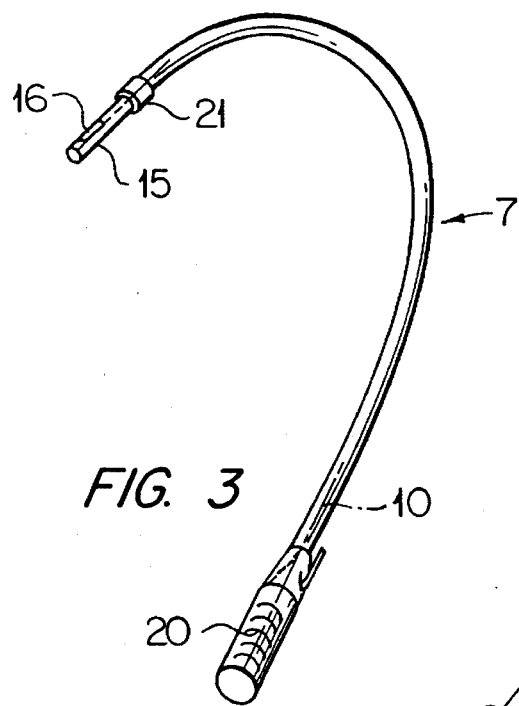
FIG. 3 is a more detailed view of one of the tubes of the invention.
Figure 5:
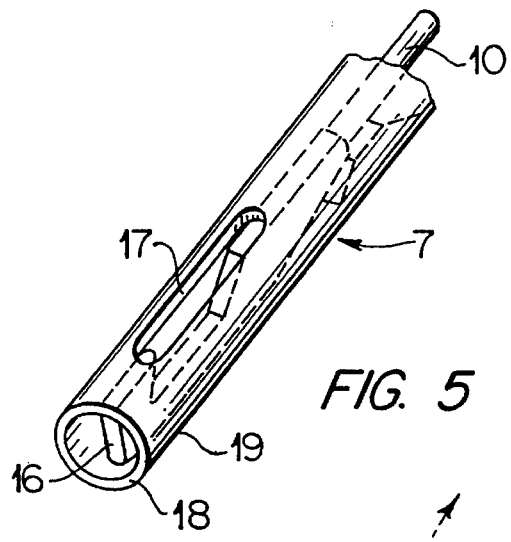
FIGS. 4 and 5 are large-scale views of the stud in the latch and the unlatched positions.
Figure 4:
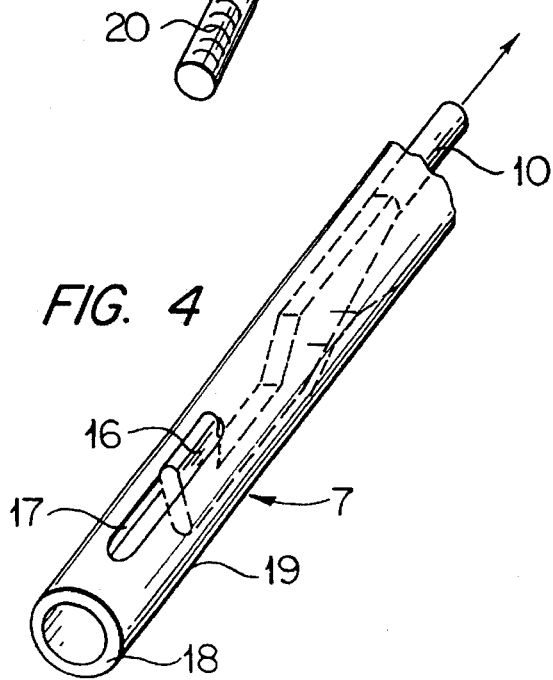

According to the invention, the assembly of the two arches is made up of two thin metal tubes 7 and 8 (FIG. 2), which are integral and intersect in front of the mouth of the patient at 9. Inside each tube, such as 7, there may slide a flexible metal wire 10 of high strength (FIGS. 3, 4 and 5). As is seen in FIG. 2, one of the wires connects the left elastic band 11 to the right molar 12 and the other connects the right elastic band 13 to the left molar 14.

Figure 7:
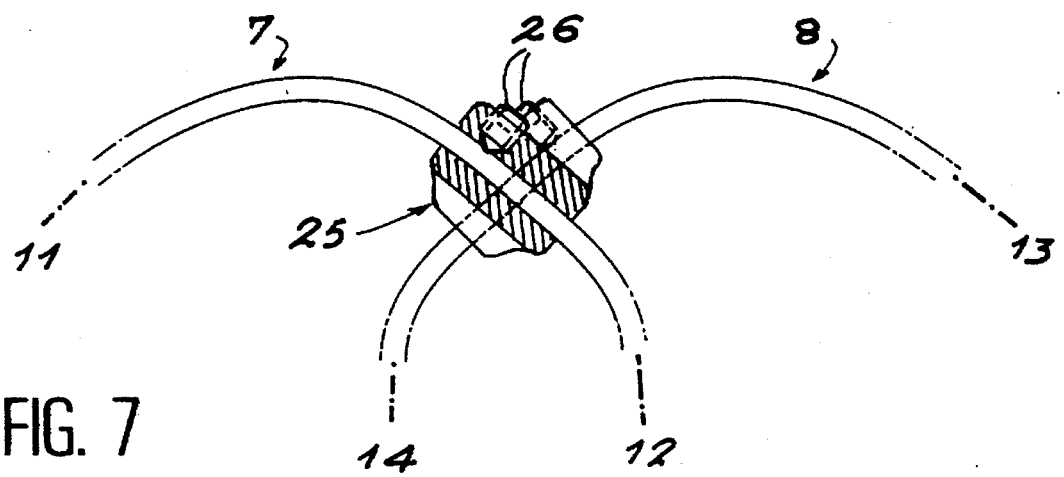
FIG. 7 is a detailed view, in partial cross-section, of the intersection of the two arches according to the invention.

At their intersection 9 the two tubes can simply be welded; but, according to the invention, they can be made integral by means of a wire grip 25 (FIG. 7); this arrangement allows the practitioner to adjust the relative lengths of the two parts 11–12 of the tube 7 and/or 13–14 of the tube 8 as a function of the forces to be applied to the apparatus, simply by loosening and tightening the two small locking screws 26.

The inner ends of the wires form, with the rings to be fixed to the molars, a latch maintained by the extra-oral force. FIG. 3 shows one such end 15 comprising a stud 16 capable of protruding (FIG. 4) into a notch 17 formed in the tube 7 between its end 18 and the distal part of the sheath 19, or else into a notch formed on the sheath of the molar (not shown); according to the invention, the stud 16 protrudes into the notch 17 when it is subjected with the wire 10 to the traction of the corresponding elastic band, and it withdraws into the inner end 18 of the tube 7 when the traction of the elastic band has disappeared (FIG. 5).

A cylindrical ring called molar stop 21 (FIG. 3) is welded onto the tube 7 which abuts against the sheath 19 when the system is put into place. This ring 21 can furthermore have a substantial length and line the tube over its entire length in order to stiffen it; the same applies, of course, to the other tube 8.

In a variant of the invention, this withdrawal of the stud 16 is effected by the action of a small spring 20 mounted at the outer end of the tube 7 and which exerts a thrust in the direction opposite to the traction of the elastic band. The small spring can just as readily be mounted inside the tube.

Figure 6:
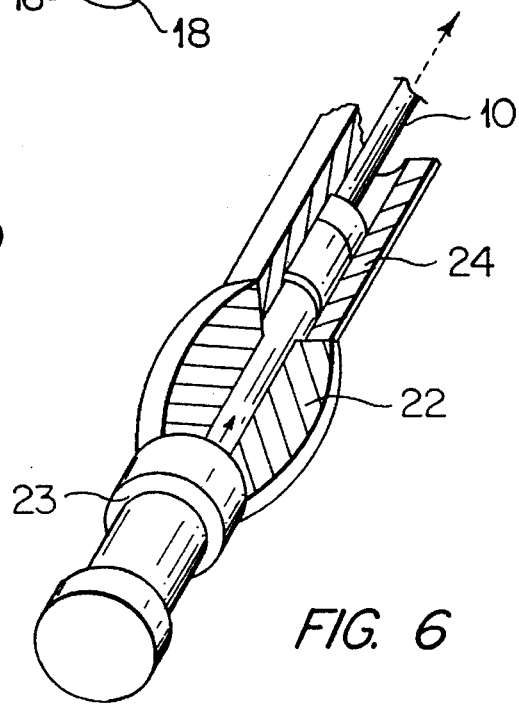
FIG. 6 is a large-scale view of the variant comprising a small elastic balloon.

According to another variant of the invention, the lock on the rings is obtained by a small sleeve 22 (FIG. 6) of general cylindrical shape, made of elastic material, mounted on the inner end of the wire, between a terminal collar 23 and the sheath 24 mounted on the ring to be fixed to the molar (not shown); the external diameter of the small sleeve 22 at rest is smaller than the internal diameter of the sheath 24; but when the small sleeve is subjected to the compression resulting from the extra-oral force, its external diameter increases and becomes greater than the internal diameter of the sheath.

Figure 8:
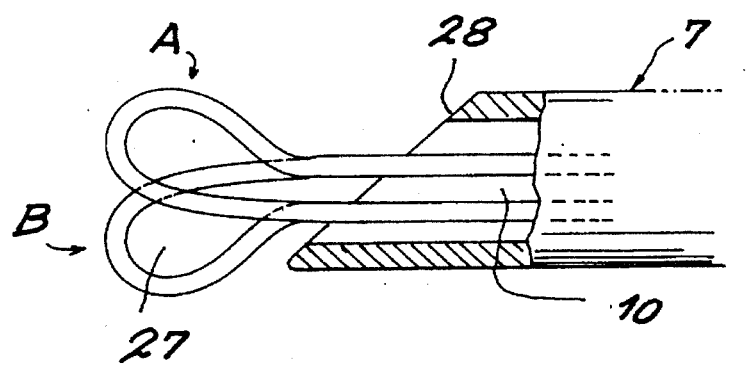
FIG. 8 is a large-scale view of the sleeve in the latched and unlatched positions.

In a preferred variant of the invention, the lock on the rings is obtained by means of a rigid loop 27 (FIG. 8) provided at the inner end of the wire 10; this loop 27 has a transverse dimension slightly smaller than the internal diameter of the tube 7. The said inner end of the tube is bevelled, as is seen at 28. When traction is exerted on the wire 10 (by the elastic bands at the other end, for example), the loop 27 engages on the bevel 28, the result of this being to offset it transversely in respect to the axis of the tube 7 and position it in abutment, thereby locking the wire 10 which then cannot escape from the tube 7. In FIG. 8, the locked position has been designated by A, and the unlocked position by B.

Figure 9:
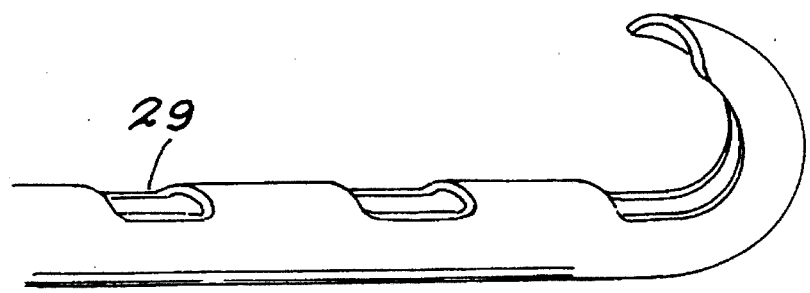
FIG. 9 is a perspective view of the slit parts of one of the tubes.

In order to avoid having tubes of several dimensions and yet to facilitate the work of the practitioner when the apparatus is put into place, it is possible to slit the tube at various positions, such as 29, in order to reduce its shear resistance, as is seen in FIG. 9.

It is quite obvious that other equivalent means can be used without departing from the scope of the present invention.

Thus, for example, all the metal elements (wires, tubes, loops, etc.) can be made of plastic material.

The latch system obtained by a (symmetrical) loop axially offset on a bevel by a traction force can be replaced by an asymmetric loop axially offset under the action of the traction force, even with the tube having a straight section.

The small latching sleeve can have various shapes, etc.

I claim:

1. A safety device for an orthodontic apparatus including an arch assembly exerting extra-oral force, and comprising:
    an inner arch having ends engaging molar rings;
    an outer arch having ends hooked to elastic bands fastened to an occipital system;
    the arches formed from two cylindrical tubes intersecting in front of a wearer's mouth;
    flexible wires slidably mounted in respective tubes;
        (a) a first wire connected between a right elastic band and a left molar ring;
        (b) the second wire connected between a left elastic band and a right molar ring;
    wherein the tube ends remain latched to the molars until the elastic bands are detached.

2. A safety device for an orthodontic apparatus as set forth in claim 1 further comprising a connector receiving the intersection of the two tubes, in bores formed perpendicularly, the tubes being adjustably received in the connector to allow adjustment in the length of each tube section relative to the intersection.

3. A safety device for an orthodontic apparatus as set forth in claim 2 wherein the latching is achieved by components connected to each tube and further comprising:
    a notch formed in an end of each tube adjacent a molar;
    a stud connected to a corresponding first end of the wire in a tube; and
    a cam for driving the stud into interference with the notch thereby latching the end of the tube to the molar when tension is applied to the wire by an elastic band, and withdrawing the stud from the notch when an elastic band is detached and tension is consequently released, thereby allowing the tube to be unlatched from the molar.

4. A safety device for an orthodontic apparatus as set forth in claim 3 further comprising a spring located at an opposite end of the wire for biasing the wire in a direction opposite the tension and causing withdrawal of the stud when the elastic band is detached.

5. A safety device for an orthodontic apparatus as set forth in claim 3 further comprising a spring located within the tube for biasing the wire in a direction opposite the tension and causing withdrawal of the stud when the elastic band is detached.

6. A safety device for an orthodontic apparatus as set forth in claim 2 wherein the latching is achieved by components associated with each tube and further comprising:
    a beveled edge formed on an end of the tube adjacent the molar thereby exposing an elliptical opening;
    a rigid loop formed on the end of the wire adjacent the molar;
    the loop having a transverse dimension slightly smaller than a shorter dimension of the opening thereby creating interference between the loop and the beveled end when tension is applied.

7. A safety device for an orthodontic apparatus as set forth in claim 2 wherein the latching is achieved by components associated with each tube and further comprising:

an asymmetric metal bulb provided formed on the end of the wire adjacent the molar;

the loop having a transverse dimension slightly smaller than the inner diameter of the tube thereby creating interference between the bulb and the tube when tension is applied.

8. A safety device for an orthodontic apparatus as set forth in claim 2 wherein the latching is achieved by components associated with each tube and further comprising:

a terminal collar mounted to the end of the wire adjacent the molar;

a substantially cylindrical and elastic sleeve, mounted between the collar and an end of the tube adjacent the molar;

the diameter of the elastic sleeve being smaller than inner diameter of the tube when no tension is applied by the wire, the diameter of the sleeve being greater than the diameter of the tube when tension is applied by the wire thereby compressingly displacing the collar against the sleeve and increasing its diameter.

* * * * *